United States Patent
Zhang et al.

(10) Patent No.: US 11,946,092 B2
(45) Date of Patent: Apr. 2, 2024

(54) METHOD FOR PRODUCING 2-KETO-3-DEOXYGLUCONATE FROM 2-(ACETYLAMINO)-2-DEOXY-D-GLUCONIC ACID BY TWO ENZYMES

(71) Applicant: SHANDONG UNIVERSITY, Jinan (CN)

(72) Inventors: Yuzhong Zhang, Jinan (CN); Pingyi Li, Jinan (CN); Wenxin Jiang, Jinan (CN); Xiulan Chen, Jinan (CN); Yishuo Zhang, Jinan (CN); Xiaoyan Song, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 18/051,024

(22) Filed: Oct. 31, 2022

(65) Prior Publication Data

US 2023/0323409 A1    Oct. 12, 2023

(51) Int. Cl.
*C12P 7/42* (2006.01)
*C12N 9/78* (2006.01)
*C12N 15/70* (2006.01)

(52) U.S. Cl.
CPC .................. *C12P 7/42* (2013.01); *C12N 9/78* (2013.01); *C12N 15/70* (2013.01); *C12Y 305/01* (2013.01); *C12Y 305/04* (2013.01); *C12N 2800/101* (2013.01)

(58) Field of Classification Search
CPC .. C12P 7/42; C12N 9/78; C12N 15/70; C12N 2800/101; C12Y 305/01; C12Y 305/04
See application file for complete search history.

(56) References Cited

PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*

* cited by examiner

*Primary Examiner* — Delia M Ramirez
(74) *Attorney, Agent, or Firm* — CBM PATENT CONSULTING, LLC

(57) ABSTRACT

A method for producing 2-keto-3-deoxygluconate (KDG) from 2-(acetylamino)-2-deoxy-D-gluconic acid (GlcNAc1A) by two enzymes; GlcNAc1A is converted to KDG by incubating GlcNAc1A with a deacetylase OngB at 25° C. for 4-12 h and then with a deaminase OngC at 25° C. for another 10-15 h; it constructs two engineered *E. coli*/pET22b-ongB (carrying the ongB gene) and *E. coli*/pET22b-ongC (carrying the ongC gene) strains to prepare recombinant proteins OngB and OngC, respectively; at the action of these two enzymes, OngB and OngC, GlcNAc1A is converted to KDG, which solves the bottleneck of GlcNAc1A utilization during the bioconversion of chitin; the KDG is an important metabolic intermediate to synthesize furan derivatives, herbicides, food additives and other industrially important chemical compounds, having wide industrial applications.

6 Claims, 5 Drawing Sheets

Specification includes a Sequence Listing.

METHOD FOR PRODUCING 2-KETO-3-DEOXYGLUCONATE FROM 2-(ACETYLAMINO)-2-DEOXY-D-GLUCONIC ACID BY TWO ENZYMES

CROSS REFERENCES

This application claims priority to Chinese Patent Application Ser. No. CN2022103676114 filed on 8 Apr. 2022.

REFERENCE TO AN ELECTRONIC SEQUENCE LISTING

The contents of the electronic sequence listing (221041JJD.xml; Size: 11,704 bytes; and Date of Creation: Oct. 27, 2022) is herein incorporated by reference in its entirety.

FIELD

The invention relates to a method for producing 2-keto-3-deoxygluconate from 2-(acetylamino)-2-deoxy-D-gluconic acid by two enzymes, belonging to the technical field of biotechnology.

BACKGROUND

To alleviate the depletion of fossil fuel resources and energy crisis, the development of efficient processes for the conversion of biomass to biofuels and other high value-added chemical compounds is crucial for creating a clean, low-carbon and sustainable economy. Chitin is the second most abundant biopolymer after cellulose in nature, which constitutes the main structural component of arthropod exoskeletons, fungal cell walls and insect cuticles. The development of efficient processes for the conversion of chitin is important for alleviating energy crisis. Chitin, an insoluble linear polysaccharide of β-1,4 linked N-acetyl-D-glucosamine (GlcNAc), is an important component of high molecular weight particulate organic matter in nature. Chitin can be degraded via chemical and biological methods. Compared to chemical degradation, biological method is preferred due to that enzymes used in this method perform catalysis under mild reaction conditions, produce fewer side-products and are biofriendly.

Recently discovered lytic polysaccharide monooxygenases (LPMOs) could oxidize the surfaces of crystalline polysaccharides to generate "nicks", allowing canonical hydrolytic enzymes to depolymerize complex biomass more efficiently. The synergistic action between LPMOs and chitinases significantly improves the degradation efficiency of recalcitrant biomass, making the LPMO an important component of commercial biomass saccharification enzyme cocktails widely used in industrial biomass conversion. Until now, all characterized chitin-active LPMOs can only oxidize the C1 carbons of glycosidic bonds in chitin to produce chitooligosaccharides with a terminal oxidized sugar, 2-(acetylamino)-2-deoxy-D-gluconic acid (GlcNAc1A). Like the oxidative degradation of cellulose, the oxidative degradation products from chitin would be eventually converted to GlcNAc and GlcNAc1A monomers catalyzed by unidentified glycoside hydrolases. Most microorganisms (e.g. *Escherichia coli*) could utilize GlcNAc and covert it to ethanol or other high value-added chemical compounds. However, most microorganisms including *E. coli* are uncapable of utilizing GlcNAc1A, leading to the low conversion efficiency of chitin. Therefore, it is necessary to explore GlcNAc1A-catabolizing enzymes to convert GlcNAc1A to an intermediate absorbed by most microorganisms.

SUMMARY OF THE INVENTION

Against the deficiency of existing technology, the present invention provides a method for producing 2-keto-3-deoxygluconate from 2-(acetylamino)-2-deoxy-D-gluconic acid by two enzymes. At the action of two enzymes including a deacetylase OngB and a deaminase OngC, GlcNAc1A, the oxidative degradation product from chitin and chitooligosaccharides, is converted to 2-keto-3-deoxygluconate (KDG), an important metabolic intermediate in bacterial carbon metabolism, to improve the conversion efficiency of chitin to ethanol and other high value-added chemical compounds The detailed description of the invention is as follows:

A method for producing 2-keto-3-deoxygluconate from 2-(acetylamino)-2-deoxy-D-gluconic acid by two enzymes is provided in which GlcNAc1A is incubated with a deacetylase OngB and a deaminase OngC for 1-24 h to generate KDG.

The preferred enzymatic reaction to produce KDG is carried out by the successive addition of a deacetylase OngB and a deaminase OngC. To produce KDG, GlcNAc1A is firstly incubated with a deacetylase OngB at 25° C. for 12 h, and then with a deaminase OngC at 25° C. for another 12 h.

The preferred molar ratio of deacetylase OngB to substrate GlcNAc1A is 1:900-1:1100.

The preferred molar ratio of deaminase OngC to deacetylase OngB is 1:9-1:11.

The recombinant deacetylase OngB is prepared from an engineered *E. coli*/pET22b-ongB strain, and the recombinant deaminase OngC is prepared from an engineered *E. coli*/pET22b-ongC strain.

The preferred host cell is *Escherichia coli* BL21 (DE3).

The nucleotide sequence of the deacetylase OngB-encoding gene is shown in SED ID NO.: 01, and the amino acid sequence of the deacetylase OngB is shown in SED ID NO.: 03.

The nucleotide sequence of the deaminase OngC-encoding gene is shown in SED ID NO.: 02, and the amino acid sequence of the deaminase OngC is shown in SED ID NO.: 04.

Engineered *E. coli*/pET22b-ongB and *E. coli*/pET22b-ongC strains are constructed involving the following steps:
 (1) The full-length gene sequence of ongB was amplified from the genomic DNA of *Pseudoalteromonas prydzensis* ACAM 620 by PCR using gene-specific primers

```
ongB_F
(5'-AAGAAGGAGATATACATATGATGCAGTACGATATCTCGCAACC
AG-3' (SEQ ID NO.: 05))
and ongB_R
(5'-TGGTGGTGGTGGTGCTCGAGATCATGTTTACTTGCTCCTAAGG
ATGTTAAAAATTG-3' (SEQ ID NO.: 06)).
```

The PCR reaction conditions were as follows: pre-denaturation at 95° C. and 30 cycles of denaturation at 95° C. for 30 s, annealing at 55° C. for 30 s, and extension at 72° C. for 1 min. The reaction was kept at 72° C. for 10 min and then stored at 16° C. The amplified fragment was ligated into the vector pET22b between the NdeI and XhoI sites to construct the recombinant plasmid pET22b-ongB.

(2) The full-length gene sequence of ongC was amplified from the genomic DNA of *Pseudoalteromonas prydzensis* ACAM 620 by PCR using gene-specific primers

```
ongC_F
(5'-AAGAAGGAGATATACATATGATGGAAAAGTTAGCCACAACAAGT
GCT-3' (SEQ ID NO.: 07))
and ongC_R
(5'-TGGTGGTGGTGGTGCTCGAGAAAATACGTATCAAAGATCTCAAT
AACGTTATAGTCATCATCT-3' (SEQ ID NO.: 08)).
```

The PCR reaction conditions were as follows: pre-denaturation at 95° C. and 30 cycles of denaturation at 95° C. for 30 s, annealing at 55° C. for 30 s, and extension at 72° C. for 1 min. The reaction was kept at 72° C. for 10 min and then stored at 16° C. The amplified fragment was ligated into the vector pET22b between the NdeI and XhoI sites to construct the recombinant plasmid pET22b-ongC.

(3) The constructed recombinant plasmid, pET22b-ongB in step (1) or pET22b-ongC in step (2), was transformed into *E. coli* BL21(DE3) competent cells to obtain an engineered *E. coli*/pET22b-ongB or *E. coli*/pET22b-ongC strain.

The deacetylase OngB and the deaminase OngC are prepared as follows:

The constructed engineered *E. coli* BL21(DE3) strains were cultured in liquid LB medium containing 100 μg/mL ampicillin at 35-40° C. and 150-200 rpm. When the $OD_{600}$ of the cultures reached 0.6-0.8, isopropyl-β-D-thiogalactopyranoside (IPTG) was added to a final concentration of 0.4-0.6 mM, and the culture was further cultivated at 15-20° C. and 100-120 rpm for 16 h. Then, the culture was centrifuged at 4° C. and 7000-10000 rpm for 5-10 min. The cells were collected, resuspended in the binding buffer (50 mM Tris-HCl, 100 mM NaCl, pH 8.0) and disrupted. The resulting extract was purified to obtain the deacetylase OngB and the deaminase OngC.

Beneficial effects in the invention:

(1) Using genes ongB and ongC from *Pseudoalteromonas prydzensis* ACAM 620, this invention constructs two engineered *E. coli*/pET22b-ongB and *E. coli*/pET22b-ongC strains to prepare recombinant proteins OngB and OngC. At the action of these two enzymes, OngB and OngC, GlcNAc1A is converted to KDG, which solves the bottleneck of GlcNAc1A utilization during the bioconversion of chitin. The produced KDG is an important metabolic intermediate to synthesize furan derivatives, herbicides, food additives and other industrially important chemical compounds, having wide industrial applications.

(2) The enzymes, OngB and OngC, provided by this invention could efficiently catalyze the conversion of GlcNAc1A to KDG, acetate and ammonia and display high substrate specificity towards GlcNAc1A, which hardly degrade GlcNAc, GlcNAc-6-P, N-acetyl-D-glutamate and N-acetyl-D-serine. The method provided by this invention uses these two enzymes, OngB and OngC, to efficiently covert GlcNAc1A into KDG, an easily metabolized intermediate by most microorganisms, which improves the conversion efficiency of chitin to ethanol and other high value-added chemical compounds and therefore has important industrial potential in biomass conversion.

DETAILED DESCRIPTION OF THE PREFERRED EMBODIMENTS

According to the present invention which represent various embodiments, these examples are offered to illustrate, but not to limit the present invention.

The genomic sequence of marine bacterium *Pseudoalteromonas prydzensis* ACAM 620 (accession no. AQHH00000000) has been deposited in the NCBI GenBank by our lab previously Example 1 Gene Cloning of ongB and ongC and Construction of Recombinant Plasmids Carrying Genes ongB and ongC Genes ongB and ongC from *Pseudoalteromonas prydzensis* ACAM 620 were ligated into the vector pET22b to construct the recombinant plasmids pET22b-ongB and pET22b-ongC, respectively. The detailed procedure was as follows:

Based on the 5' end and 3' end sequences of genes ongB and ongC, two primer pairs were designed,

```
ongB_F
(5'-AAGAAGGAGATATACATATGATGCAGTACGATATCTCGCAACCA
G-3' (SEQ ID NO.: 05))
and ongB_R
(5'-TGGTGGTGGTGGTGCTCGAGATCATGTTTACTTGCTCCTAAGGA
TGTTAAAAATTG-3' (SEQ ID NO.: 06))
``` for gene cloning of ongB, and

```
ongC_F
(5'-
AAGAAGGAGATATACATATGATGGAAA AGTTAGCCACAACAAGTGCT-
3' (SEQ ID NO.: 07))
and
```

-continued ongC_R
(5'-TGGTGGTGGTGGTGCTCGAGAAAATA
CGTATCAAAGATCTCAATAACGTTATAGTCATCATCT-3' (SEQ
ID NO.: 08))

for gene cloning of ongC. With these primers and the genomic DNA of *Pseudoalteromonas prydzensis* ACAM 620 as the template, PCR amplification was performed with the following procedure: pre-denaturation at 95° C. and 30 cycles of denaturation at 95° C. for 30 s, annealing at 55° C. for 30 s, and extension at 72° C. for 1 min. The reaction was kept at 72° C. for 10 min and then stored at 16° C. An about 1.4 kb DNA fragment of ongB and an about 1.2 kb DNA fragment of ongC were amplified. The amplified fragments were ligated into the vector pET22b between the NdeI and XhoI sites to construct the recombinant plasmids pET22b-ongB and pET22b-ongC. The constructed recombinant plasmids, pET22b-ongB and pET22b-ongC, were transformed into *E. coli* DH5α competent cells by using the heat shock method to obtain recombinant strains DH5α/pET22b-ongB and DH5α/pET22b-ongC, respectively. The constructed recombinant *E. coli* strains were cultured in liquid LB medium containing 100 μg/mL ampicillin at 37° C. overnight. Plasmids pET22b-ongB and pET22b-ongC were extracted from cultured cells and sequenced, respectively. The results showed that the ongB gene as shown in SEQ ID NO.1 and the ongC gene as shown in SEQ ID NO.2 were successfully inserted between the NdeI and XhoI restriction sites of pET22b in the correct direction.

Example 2 Construction of Recombinant *E. coli* Strains

Figure 1:
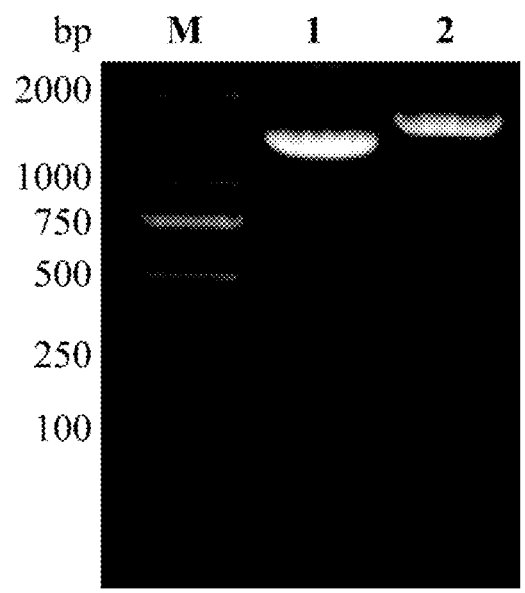
FIG. 1. Gel electrophoresis of amplified gene fragments of ongB and ongC. Lane M, DNA molecular weight marker; lane 1, amplified gene fragment of ongC; lane 2, amplified gene fragment of ongB.

Recombinant plasmids pET22b-ongB and pET22b-ongC were transformed into *E. coli* BL21(DE3) to obtain engineered *E. coli*/pET22b-ongB and *E. coli*/pET22b-ongC strains, respectively. The detailed procedure was as follows:

The constructed recombinant plasmids pET22b-ongB and pET22b-ongC in Embodiment 1 were transformed into *E. coli* BL21 (DE3) competent cells by using the heat shock method described in "Molecular Cloning: A Laboratory Manual". The resultant cells were spread onto LB plates containing 100 μg/mL ampicillin and cultured at 37° C. overnight. Colony PCR was then carried out using a single colony of *E. coli*/pET22b-ongB or *E. coli*/pET22b-ongC as the template. The results showed that the target DNA fragments obtained from single colonies of *E. coli*/pET22b-ongB and *E. coli*/pET22b-ongC exactly match the length of genes ongB and ongC respectively (FIG. 1), suggesting that engineered *E. coli*/pET22b-ongB and *E. coli*/pET22b-ongC strains are successfully constructed.

Example 3 Heteroexpression and Purification of Recombinant Proteins OngB and OngC Single colonies of engineered *E. coli*/pET22b-ongB and *E. coli*/pET22b-ongC strains in Embodiment 2 were inoculated into LB liquid medium containing 100 μg/mL ampicillin and cultured at 37° C. and 180 rpm. When the $OD_{600}$ of the cultures reached 0.6-0.8, isopropyl-β-D-thiogalactopyranoside (IPTG) was added to a final concentration of 0.5 mM, and the culture was further cultivated at 18° C. and 110 rpm for 16 h. Then, the culture was centrifuged at 8000 rpm at 4° C. for 5-10 min. The cells were collected, resuspended in the binding buffer (50 mM Tris-HCl, 100 mM NaCl, pH 8.0) and disrupted by high pressure cell cracker. The recombinant proteins in the resulting extract were purified with Ni-nitrilotriacetic acid (NTA) resin and desalted with PD-10 desalting columns. SDS-PAGE analysis suggested that recombinant proteins OngB and OngC with high purity were obtained (FIG. 2).

Figure 2:
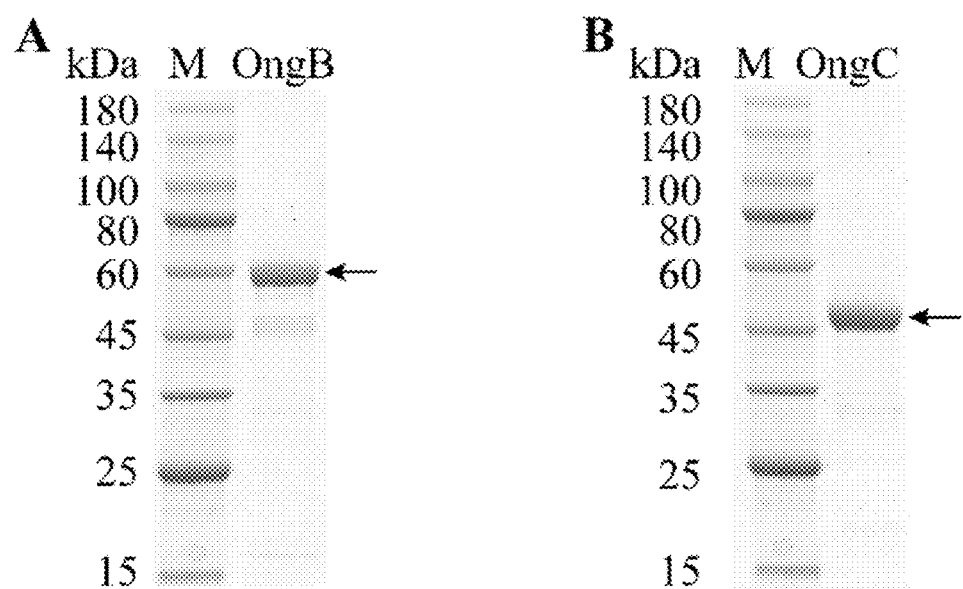
FIG. 2. SDS-PAGE analysis of purified recombinant proteins, OngB and OngC. A, SDS-PAGE analysis of purified recombinant OngB (marked by an arrow). Lane M, protein molecular weight marker. B, SDS-PAGE analysis of purified recombinant OngC (marked by an arrow). Lane M, protein molecular weight marker.

As shown in FIG. 2, the purified OngB from *E. coli*/pET22b-ongB displayed an apparent molecular weight of approximately 53 kDa, and the purified OngC from *E. coli*/pET22b-ongC displayed an apparent molecular weight of approximately 45 kDa, consistent with their calculated molecular masses.

Example 4 Production of 2-keto-3-deoxygluconate from 2-(acetylamino)-2-deoxy-D-gluconic acid Catalyzed by Two Enzymes, OngB and OngC A method for producing KDG from GlcNAc1A by two enzymes involves these steps as follows:

(1) A reaction mixture containing 10 μM OngB, 10 mM GlcNAc1A, and 10 mM Bis-Tris-HCl buffer (pH 7.5) was incubated at 25° C. for 12 h. The resulting mixture was then centrifuged at 13,000 rpm for 10 min and the supernatant containing product 1 was obtained.

(2) A reaction mixture containing 1 μM OngC, 10 mM product 1 prepared in step (1), and 10 mM Bis-Tris-HCl buffer (pH 7.5) was incubated at 25° C. for 12 h. The resulting mixture was then centrifuged at 13,000 rpm for 10 min and the supernatant containing product 2 was obtained.

The obtained products 1 and 2 were analyzed with High-Resolution Q-TOF mass spectrometry (Q-TOF-MS) for m/z determination. For MS analysis, the following operating parameters were used: drying $N_2$ gas flow rate, 4 l/min; temperature, 180° C.; nebulizer pressure, 6 psi; capillary, 4,500 V; and End Plate Offset, 500 V. The acquisition mass range used was from m/z 50 to 1,500 in negative ion mode.

Figure 3:
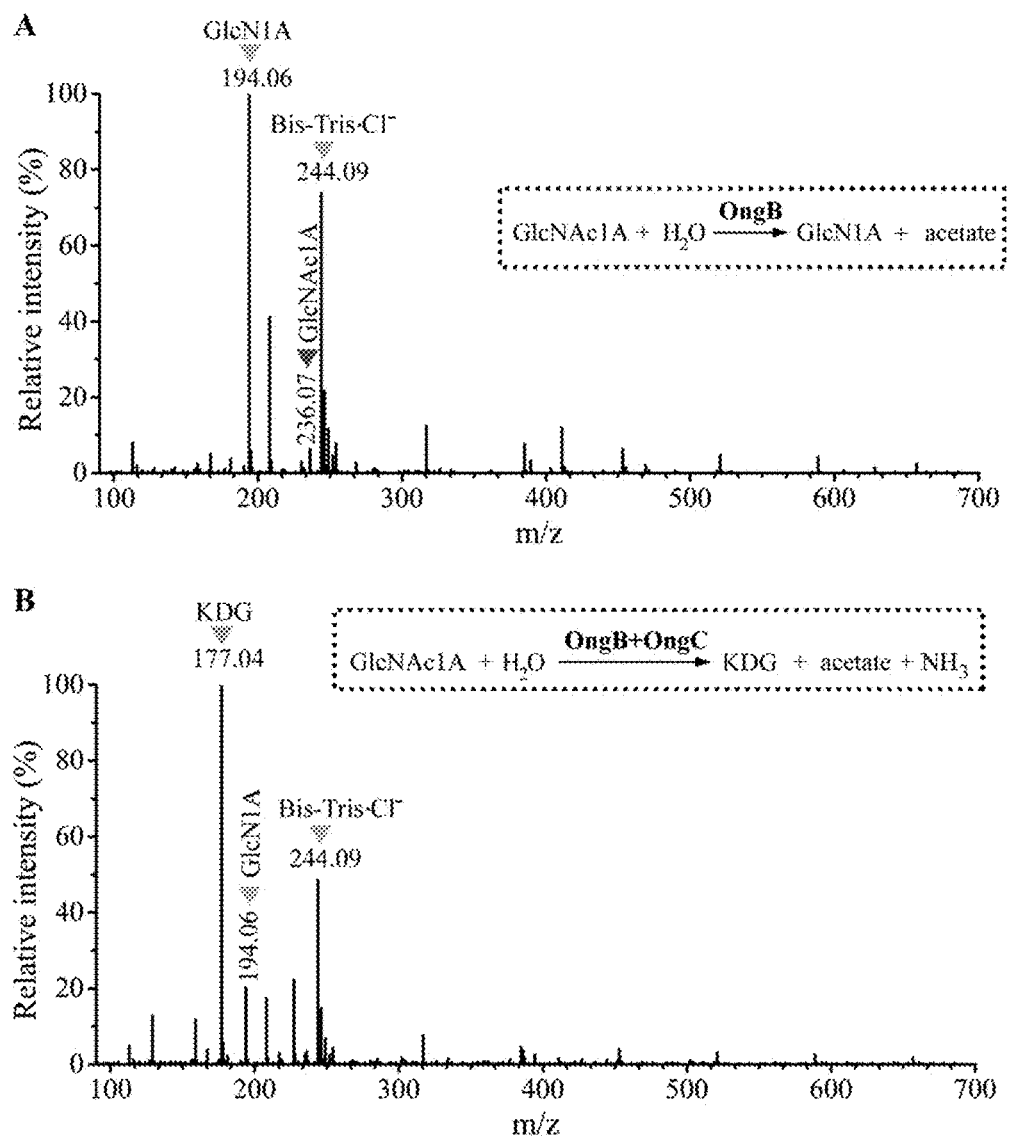
FIG. 3. Q-TOF-MS analysis of products generated by the recombinant enzymes, OngB and OngC, acting on GlcNAc1A. A, Q-TOF-MS analysis of products generated by the recombinant OngB acting on GlcNAc1A. B, Q-TOF-MS analysis of products generated by OngB and OngC acting on GlcNAc1A.

As shown in FIG. 3A, product 1 is 2-(amino)-2-deoxy-D-gluconic acid (GlcN1A), suggesting that OngB can deacetylate GlcNAc1A to GlcN1A.

As shown in FIG. 3B, product 2 is KDG, suggesting that at the action of these two enzymes, OngB and OngC, GlcNAc1A is converted to KDG Therefore, using genes ongB and ongC from *Pseudoalteromonas prydzensis* ACAM 620, this invention constructs two engineered *E. coli*/pET22b-ongB and *E. coli*/pET22b-ongC strains to prepare recombinant proteins OngB and OngC. At the action of these two enzymes, OngB and OngC, GlcNAc1A is converted to KDG.

Example 5 Substrate Specificity Analysis of OngB and OngC (1) Substrate Specificity Analysis of OngB Substrate specificity assays were performed with GlcNAc1A, GlcNAc, GlcNAc-6-P, N-acetyl-D-glutamate and N-acetyl-D-serine. Standard reaction system contained 5 μM OngB, 25 mM substrate and 10 mM Bis-Tris-HCl (pH 7.5). Reactions were conducted at 25° C. for 30 min. The production of acetate in the reaction mixture was determined with an Acetic Acid (ACS Analyser Format) Assay Kit. One unit of enzyme (U) is defined as the amount of enzyme required to release 1 μmol of acetate per minute.

Figure 4:
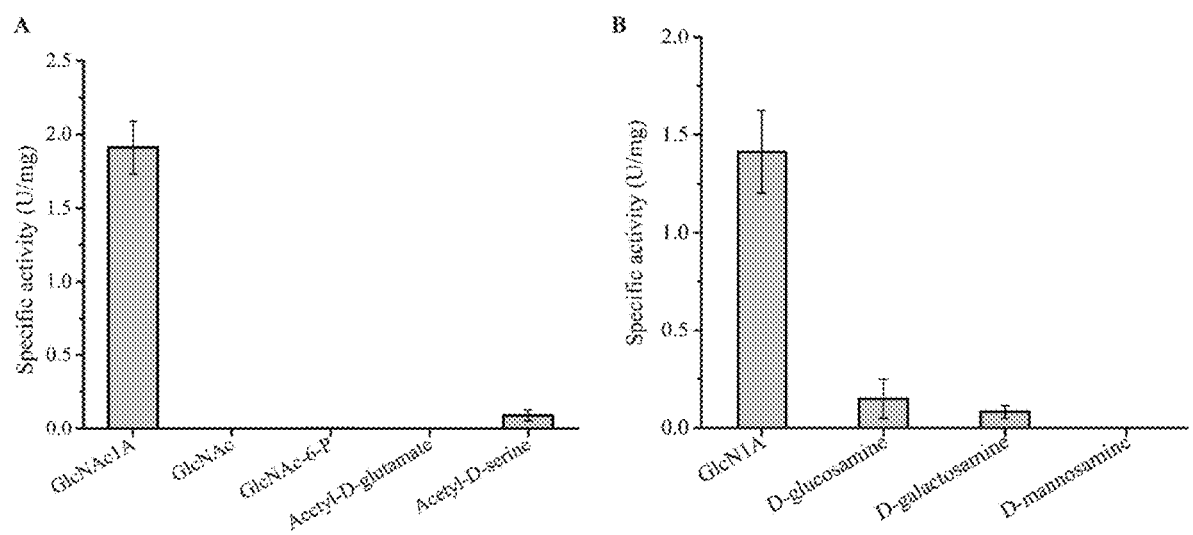
FIG. 4. Substrate specificity analysis of OngB and OngC. A, Substrate specificity analysis of the deacetylase OngB. B, Substrate specificity analysis of the deaminase OngC.

As shown in FIG. 4A, OngB displays high substrate specificity towards GlcNAc1A, and little or no activity for GlcNAc, GlcNAc-6-P, N-acetyl-D-glutamate and N-acetyl-D-serine.

(2) Substrate Specificity Analysis of OngC

Substrate specificity assays were performed with GlcN1A, D-glucosamine, D-galactosamine and D-mannosamine. GlcN1A was prepared by incubating 10 μM OngB with 10 mM GlcNAc1A in 10 mM Bis-Tris-HCl (pH 7.5) at 25° C. for 4 h. Standard reaction system contained 0.5 μM OngC, 10 mM substrate and 10 mM Bis-Tris-HCl (pH 7.5). Reactions were conducted at 25° C. for 30 min. The production of ammonia in the reaction mixture was determined with an AMMONIA (Rapid) ASSAY PROCEDURE. One unit of enzyme (U) is defined as the amount of enzyme required to release 1 μmol of ammonia per minute.

As shown in FIG. 4B, OngC displays high substrate specificity towards GlcN1A, and little or no activity for D-glucosamine, D-galactosamine and D-mannosamine.

Example 6 Sequence Analysis of OngB and OngC (1) Sequence Analysis of OngB

Among characterized enzymes, OngB is most closely related to the D-aminoacylase (accession no. 1RJP) from *Alcaligenes faecalis*, sharing 46% sequence identity. To analyze the relationships between OngB and other de-N-acetylases, homologs to OngB, characterized N-acetyl-D-amino acid deacetylases (including N-acetyl-D-glutamate deacetylases (Acetyl-D-Glu DA) and acetylcitrulline deacetylases (Acetylcitrulline DA)), and characterized carbohydrate de-N-acetylases (including GlcNAc deacetylases (GlcNAc DA), GlcNAc-6-P deacetylases (GlcNAc-6-P DA), chitin deacetylases (Chitin DA), peptidoglycan N-acetylglucosamine deacetylases (PGN GlcNAc DA), chitooligosaccharide deacetylases (Chitooligosaccharide DA), galactoaminogalactan deacetylases (Galactoaminogalactan DA) and UDP-GlcNAc deacetylases (UDP-GlcNAc DA)) were downloaded from the NCBI nr database. OngB and its homologs and characterized de-N-acetylases were aligned by MUSCLE with a WAG-based model and visualized using Molecular Evolutionary Genetics Analysis version 7.0 (MEGA7).

Figure 5:
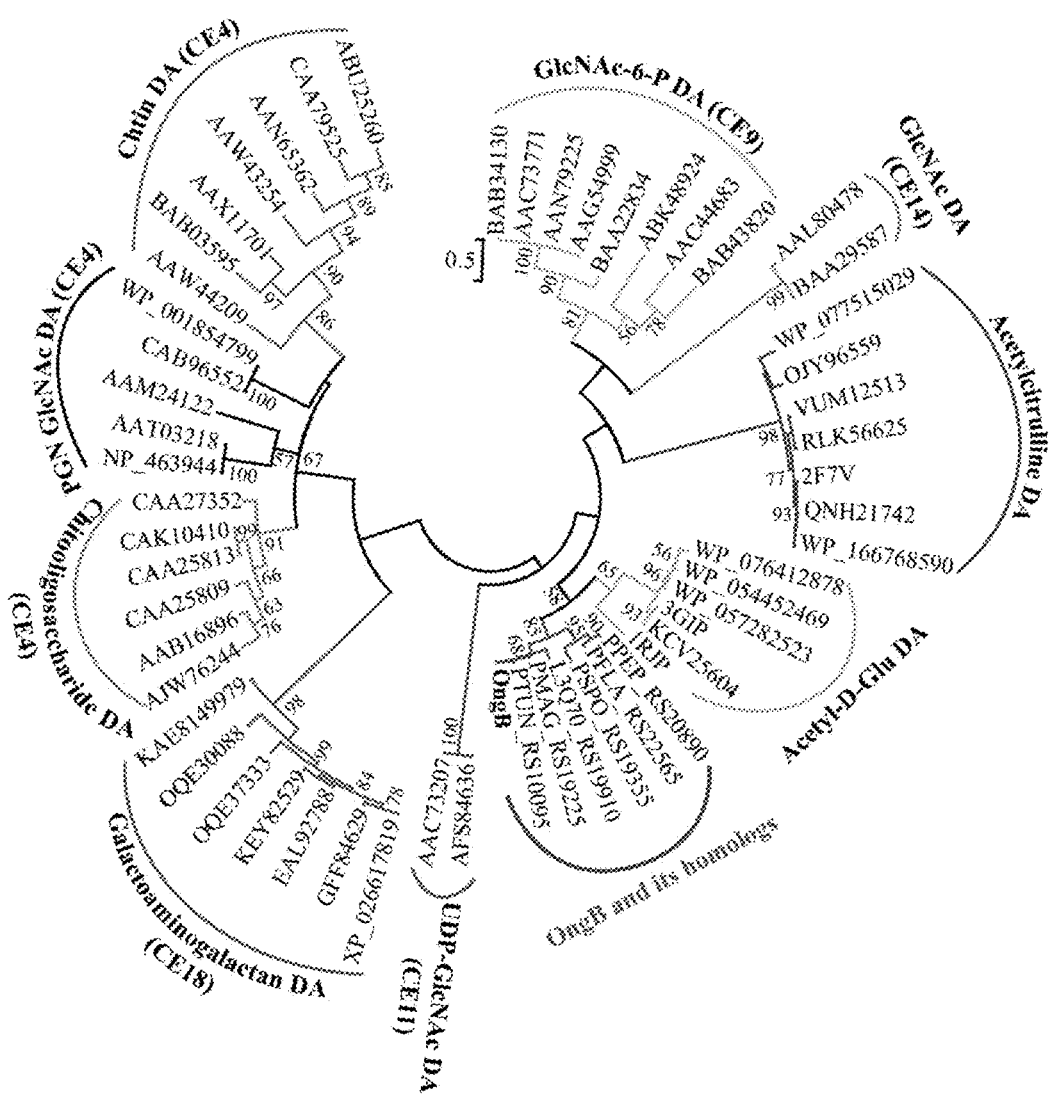
FIG. 5. Phylogenetic analysis of OngB and its homologs and other de-N-acetylases.

As shown in FIG. 5, OngB and its homologs from the ONG clusters of bacteria are clustered as a separate group from all characterized de-N-acetylases in the phylogenetic tree, suggesting that OngB and its homologs may represent a new de-N-acetylase family. Compared to carbohydrate de-N-acetylases, OngB and its homologs are more closely related to N-acetyl-D-glutamate deacetylases (Acetyl-D-Glu DA). However, substrate specificity analysis showed that OngB hardly degraded N-acetyl-D-amino acids while displaying high substrate specificity towards GlcNAc1A (FIG. 4A).

(2) Sequence Analysis of OngC

Among characterized enzymes, OngC is most closely related to the D-threonine aldolase (24% identity) from *Achromobacter xylosoxidans*. To reveal the evolutionary position of OngC, homologs to OngC, characterized D-amino acid deaminases (including D-serine dehydratases and D-serine dehydratases DSD1) and characterized D-threonine aldolases were downloaded from the NCBI nr database. OngC and its homologs and characterized pyridoxal 5-phosphate (PLP)-dependent enzymes were aligned by MUSCLE with a JTT-matrix-based model and visualized using Molecular Evolutionary Genetics Analysis version 7.0 (MEGA7).

Figure 6:
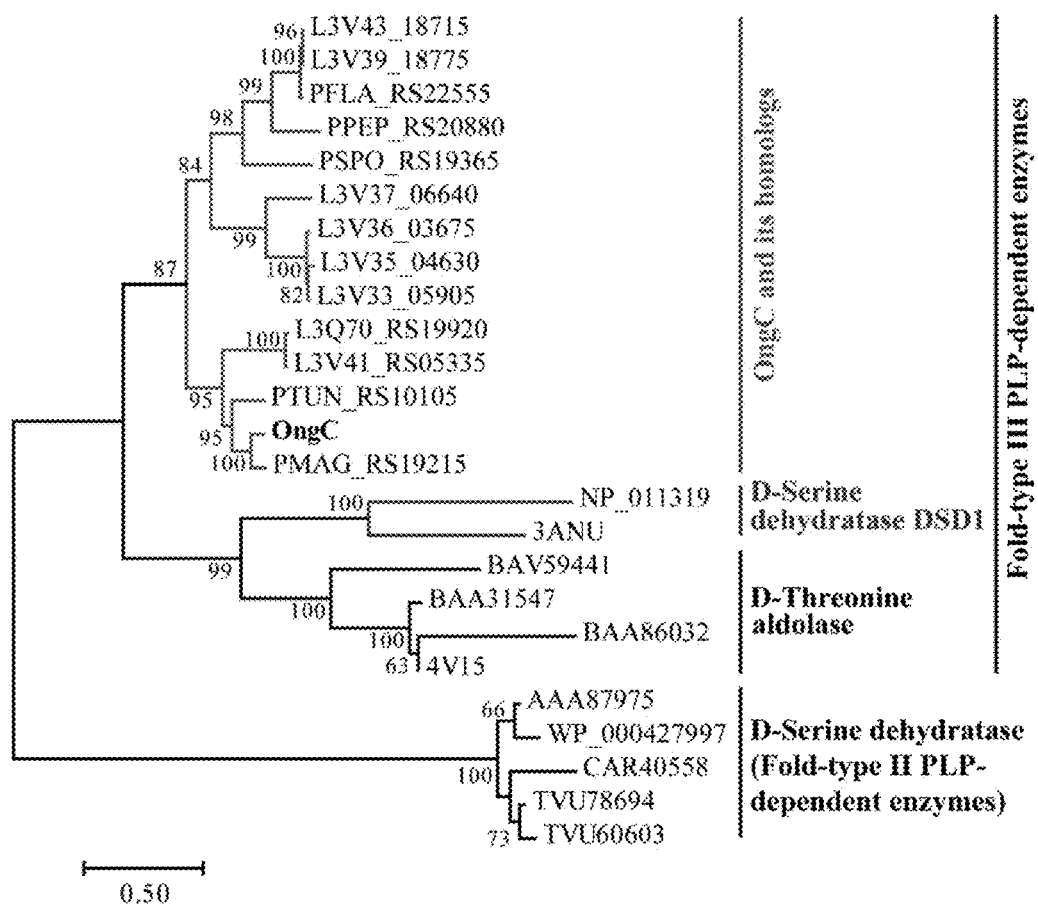
FIG. 6. Phylogenetic analysis of OngC and its homologs and characterized pyridoxal 5-phosphate (PLP)-dependent enzymes.

As shown in FIG. 6, OngC and its homologs from the ONG clusters of bacteria, D-serine dehydratases DSD1 and D-threonine aldolases all belong to the Fold-type III PLP-dependent enzyme superfamily. However, OngC and its homologs form a separate clade of the Fold-Type III PLP-dependent enzyme superfamily, suggesting that OngC and its homologs may represent a new family of the Fold-Type III PLP-dependent enzyme superfamily. Substrate specificity analysis showed that OngC displays high substrate specificity towards GlcN1A (FIG. 4B).

In summary, at the action of two enzymes including a deacetylase OngB and a deaminase OngC, GlcNAc1A, the oxidative degradation product from chitin and chitooligosaccharides, can be converted to KDG, an easily metabolized intermediate by most microorganisms, which not only provides a new method for preparing KDG, but also improves the conversion efficiency of chitin to ethanol and other high value-added chemical compounds. Therefore, the method provided by this invention has important industrial potential in the preparation of KDG and related derivatives and biomass conversion.

What is claimed is:

1. A method for producing 2-keto-3-deoxygluconate (KDG) from 2-(acetylamino)-2-deoxy-D-gluconic acid (GlcNAc1A), wherein said method comprises contacting GlcNAc1A with a deacetylase having the amino acid sequence of SEQ ID NO: 3 and a deaminase having the amino acid sequence of SEQ ID NO: 4 for 1-24 h to generate KDG.

2. The method according to claim 1, wherein the method for producing KDG is carried out by the successive addition of the deacetylase and the deaminase, wherein GlcNAc1A is first incubated with the deacetylase at 25° C. for 12 h, and then with the deaminase at 25° C. for another 12 h.

3. The method according to claim 1, wherein the molar ratio of the deacetylase to GlcNAc1A is 1:900-1:1100.

4. The method according to claim 1, wherein the molar ratio of the deaminase to the deacetylase is 1:9-1:11.

5. The method according to claim 1, wherein the deacetylase is encoded by a deacetylase DNA having the nucleotide sequence of SEQ ID NO: 1.

6. The method according to claim 1, wherein the deaminase is encoded by a deaminase DNA having the nucleotide sequence of SEQ ID NO: 2.

* * * * *

SEQUENCE LISTING

```
Sequence total quantity: 8
SEQ ID NO: 1           moltype = DNA  length = 1470
FEATURE                Location/Qualifiers
source                 1..1470
                       mol_type = other DNA
                       organism = Pseudoalteromonas prydzensis
SEQUENCE: 1
atgcagtacg atatctcgca accagtagac acaatcatct atcaagcaaa ggtatttgat   60
ggcttaggta atgcgccagt gcacatggac gttgcaatta aagggcagca gattgtcgca  120
ctgggggagt tatcagcata ccaagcaaca gaggaagtga atgccgatgg attgtgttta  180
gcgccaggct ttattgatgt acatactcac gatgatttag aagtactcag aaaccctgaa  240
atggcggcta aaataagcca aggagtgact accgttatta caggaaattg tggcattagt  300
gcagcacctg ccgagttagc caatgatgcg ccagatccaa tgaacctctt aggtgaaaaa  360
gctgaattta aatttgccca gctgcgcgat tatatcgacg cctacaaggt gcaaaaagcc  420
aacgtaaatg tggctgcctt agttggccat accacgctta gaataatgt gatggccgac  480
ttattacgcc cagcgacagc cgcagaaatc accttaatgc agcagcaact tgaccttgca  540
ctgagtcaag gcgcattagg cttgagtact ggccttgcct ataaaaatgc taatcaggcg  600
ccatcctctg aagtgcacgc gttttggtgaa gtgttgaaaa aacacgatgc gctgtatacc  660
acacatttac gcaccgagtt tgacgcagta cttgatgcaa tggacgaagc ctttgcgatg  720
gagcaagcat tcgatattaa ggtgattatt tcgcaccctta aatgcgcagg taaaaataac  780
tgggggcggg ctcctgaatt attggctaaa ttttctgagc aaggtgagca ttcaaaatgc  840
agttgtgacg cttaccgta tgccgcaagt tccagcacct tagatttaaa ccaagtgacc  900
gatgattttg atatttttat aacctggtct gattctcatc ctgaaatggc ggaacaatta  960
ctggccgata ttgctaagca gtggggggatt agtttgcttg atgcagctaa acaactgcaa 1020
cccgcgggag cggtttatca tggccttaat gaagacgatg taaaaaccat tctcgcgttt 1080
```

```
gataaaacca tgattggctc cgacggctta ccgtgcgatc cccatccgca tccgcgttta   1140
tggggctcat ttcctcgggt tttaggtcat tatagccgtg agcaaggcat ttttccttg    1200
gctacagcaa ttcataaaat gaccggttta agcgcagcaa attaccggtt agcaaaccgt   1260
ggggtgatca aggtgggtca ttttgctgat ttagtattat ttgatgccga tgaaattatt   1320
gataacgcga cctttgttga atctgcctta ccggcatcgg gtattcatca ggtttggact   1380
aatggccaaa ccacatttaa agataaacga gtttacccg  cgtattcggg tcaattttta   1440
acatccttag gagcaagtaa acatgattag                                    1470

SEQ ID NO: 2            moltype = DNA  length = 1248
FEATURE                 Location/Qualifiers
source                  1..1248
                        mol_type = other DNA
                        organism = Pseudoalteromonas prydzensis
SEQUENCE: 2
atggaaaagt tagccacaac aagtgctgaa aatatcgcaa gtgtgaataa aggcttaggt    60
aatgatgagg cactcataca tgaggattgc aatgttgctt tgcagcaagt cagttttgcct  120
tgtgcatgta tttaccaaac tcggttagat aataacattg cgtggatggc aaagtttgcg   180
cagcaaagta aggtggagtt ttcaccccat ggtaaaacca ctatggcacc tggtatttt   240
aaaaagcagt taaatgcagg tgcttacgcg atcactattg caacggtaca acaggctgtg   300
gtggctgctc gcgctggtgc aaagcgtatt attatggcga atcaattagt tggcaaagcc   360
aacatgcagc agcttagcta tttattaaaa cagtataaga ttgattttta ttgtttagtg   420
gatgatgtta gtaatgtaac aaggcttggt gagttttta gcgaacaagg tttacagctt    480
aaattactga ttgagctagg agtgcctggc ggacgttgtg gtgttgttga taatcaaact   540
cttcagcaat tggctgcgca tattcaacag tttgcttcat tacagcttgc gggtattgaa   600
gtgtatgaag gcgtattgag tacacaaagt gaagtgactg cattttttagc agatgcggta   660
gcaaaatgta aagttttgat tgaaaagcag gcttttgcta cagagcaagt gatcattacc   720
gctggtggct ctgcttggta tgacttagtg tgtgatgcat ttgcaccgca caacttgtta   780
gacaacatga tacctgtgat ccgccctgga tgttacgttg cccatgatca aggaatatat   840
gagcacgcac agcagcaagt attagcgcgc aatccgctgg catgcaatat tggtagtgac   900
ttacagtcgt gcctagagat ttgggcgtat gtgcaatcat tgccagagcc tggtcgtgcc   960
attattggta tgggtaaacg agatgtcgcc ttcgatgccg gtttacccat tgccaattta  1020
catgtggatc aatcaggcac cgtaaaacct gcggggccg attggaaagt agaaaaaata   1080
atggatcagc acgcgatgct gacttatacc ggcacagaac aactaaaagt gggcgatatt   1140
atagcatttg caacttcgca cccatgcctt acattcgata aatggcgttt tattaacgtc   1200
atagatgatg actataacgt tattgagatc tttgatacgt attttttag                1248

SEQ ID NO: 3            moltype = AA   length = 489
FEATURE                 Location/Qualifiers
source                  1..489
                        mol_type = protein
                        organism = Pseudoalteromonas prydzensis
SEQUENCE: 3
MQYDISQPVD TIIYQAKVFD GLGNAPVHMD VAIKGQQIVA LGELSAYQAT EEVNADGLCL    60
APGFIDVHTH DDLEVLRNPE MAAKISQGVT TVITGNCGIS AAPAELANDA PDPMNLLGEK   120
AEFKFAQLRD YIDAYKVQKA NVNVAALVGH TTLRNNVMAD LLRPATAAEI TLMQQQLDLA   180
LSQGALGLST GLAYKNANQA PSSEVHAFGE VLKKHDALYT THLRTEFDAV LDAMDEAFAM   240
EQAFDIKVII SHLKCAGKNN WGRAPELLAK FSEQGEHSKC SCDAYPYAAS SSTLDLNQVT   300
DDFDIFITWS DSHPEMAEQL LADIAKQWGI SLLDAAKQLQ PAGAVYHGLN EDDVKTILAF   360
DKTMIGSDGL PCDPHPHPRL WGSFPRVLGH YSREQGIFSL ATAIHKMTGL SAANYRLANR   420
GVIKVGHFAD LVLFDADEII DNATFVESAL PASGIHQVWT NGQTTFKDKR VLPAYSGQFL   480
TSLGASKHD                                                           489

SEQ ID NO: 4            moltype = AA   length = 415
FEATURE                 Location/Qualifiers
source                  1..415
                        mol_type = protein
                        organism = Pseudoalteromonas prydzensis
SEQUENCE: 4
MEKLATTSAE NIASVNKGLG NDEALIHEDC NVALQQVSLP CACIYQTRLD NNIAWMAKFA    60
QQSKVEFSPH GKTTMAPGIF KKQLNAGAYA ITIATVQQAV VAARAGAKRI IMANQLVGKA   120
NMQQLSYLLK QYKIDFYCLV DDVSNVTRLG EFFSEQGLQL KLLIELGVPG GRCGVVDNQT   180
LQQLAAHIQQ FASLQLAGIE VYEGVLSTQS EVTAFLADAV AKCKVLIEKQ AFATEQVIIT   240
AGGSAWYDLV CDAFAPHNLL DNMIPVIRPG CYVAHDQGIY EHAQQQVLAR NPLACNIGSD   300
LQSCLEIWAY VQSLPEPGRA IIGMGKRDVA FDAGLPIANL HVDQSGTVKP AGADWKVEKI   360
MDQHAMLTYT GTEQLKVGDI IAFATSHPCL TFDKWRFINV IDDDYNVIEI FDTYF        415

SEQ ID NO: 5            moltype = DNA  length = 45
FEATURE                 Location/Qualifiers
source                  1..45
                        mol_type = other DNA
                        organism = synthetic construct
SEQUENCE: 5
aagaaggaga tatacatatg atgcagtacg atatctcgca accag                    45

SEQ ID NO: 6            moltype = DNA  length = 56
FEATURE                 Location/Qualifiers
source                  1..56
                        mol_type = other DNA
                        organism = synthetic construct
```

```
SEQUENCE: 6
tggtggtggt ggtgctcgag atcatgttta cttgctccta aggatgttaa aaattg         56

SEQ ID NO: 7            moltype = DNA  length = 47
FEATURE                 Location/Qualifiers
source                  1..47
                        mol_type = other DNA
                        organism = synthetic construct
SEQUENCE: 7
aagaaggaga tatacatatg atggaaaagt tagccacaac aagtgct                   47

SEQ ID NO: 8            moltype = DNA  length = 63
FEATURE                 Location/Qualifiers
source                  1..63
                        mol_type = other DNA
                        organism = synthetic construct
SEQUENCE: 8
tggtggtggt ggtgctcgag aaaatacgta tcaaagatct caataacgtt atagtcatca     60
tct                                                                   63
```